United States Patent [19]
Collinge et al.

[11] Patent Number: 6,090,550
[45] Date of Patent: Jul. 18, 2000

[54] AUTOMATED DNA SEQUENCING COMPARING PREDICTED AND ACTUAL MEASUREMENTS

[75] Inventors: John Collinge, London; David Thornley, Perivale, both of United Kingdom

[73] Assignee: Imperial College of Science, Technology and Medicine, London, United Kingdom

[21] Appl. No.: 08/860,050

[22] PCT Filed: Dec. 22, 1995

[86] PCT No.: PCT/GB95/03026

§ 371 Date: Aug. 28, 1997

§ 102(e) Date: Aug. 28, 1997

[87] PCT Pub. No.: WO96/20286

PCT Pub. Date: Jul. 4, 1996

[30] Foreign Application Priority Data

Dec. 23, 1994 [GB] United Kingdom .................... 9426223
Feb. 22, 1995 [GB] United Kingdom .................... 9503526

[51] Int. Cl.[7] .............................. C12Q 1/68; C12P 19/34; G01N 33/00
[52] U.S. Cl. ................................ 435/6; 435/91.1; 436/94
[58] Field of Search .......................... 435/6, 91.1; 436/94

[56] References Cited

U.S. PATENT DOCUMENTS

| 4,941,092 | 7/1990 | Hara et al. | 364/413.15 |
| 4,958,281 | 9/1990 | Hara et al. | 364/413.01 |

FOREIGN PATENT DOCUMENTS

| 213 537 | 3/1987 | European Pat. Off. . |
| 242 629 | 10/1987 | European Pat. Off. . |
| 0 478450 | 4/1992 | European Pat. Off. . |
| 0 514 927 A1 | 11/1992 | European Pat. Off. . |
| WO 92/02635 | 2/1992 | WIPO . |

OTHER PUBLICATIONS

Genomics, vol. 19, No. 3, Feb. 1994, San Diego, US, pp. 417–424, XP000568813 Lipshutz et al.: "DNA Sequence confidence estimation".

Nature, vol. 365, Oct. 1993, London, GB, pp. 671–673, XP002001715 Larder et al.: "Quantitative detection of HIV–1 drug resistance mutations by automated DNA sequencing".

Nucleic Acids Research, vol. 20, No. 10, 1992, Oxford GB, pp. 2471–1483, XP002001716 Lee et al.: "DNA sequencing with dye labeled terminators and T7 polymerase".

Nucleic Acids Research, vol. 21, No. 19, 1993, Oxford GB, pp. 4530–4540, XP002001717 Giddings M C; Brumley R L Jr; Haker M; Smith L M: "An adaptive, object oriented strategy for base calling in DNA sequence analysis".

*Primary Examiner*—Kenneth R. Horlick
*Attorney, Agent, or Firm*—Nixon & Vanderhye P.C.

[57] ABSTRACT

A method of automatically sequencing DNA comprises repeatedly determining the next base in the sequence as a function not only of a physical measurement made at that position, but also as a function of previously-determined near-by bases in the same sequence. Typically, a computer algorithm is used which predicts the value of the expected measurement at a given position based upon a knowledge of the bases in previous and/or subsequent positions. The predicted measurement is then compared with the actual measurement, and the base chosen at that position is the base which minimizes the accumulated error measure for the entire sequence. The preferred algorithm, which may be parallel or sequential, preferably includes physical modelling of the replication effect and of the fluorescence effect.

46 Claims, 2 Drawing Sheets

AUTOMATED DNA SEQUENCING COMPARING PREDICTED AND ACTUAL MEASUREMENTS

The present invention relates to automated DNA sequencing.

The most commonly used DNA sequencing technique used at the present time is due to Sanger et al, and was first discussed in Sanger, F., Nicklen, S. and Coulson, A. R. (1977): DNA sequencing with chain-terminating inhibitors. Proc. Natl. Acad. Sci. USA 74; 5463–5467. Variations of Sanger's technique have revolutionised genome analysis by enabling rapid and reasonably accurate determination of unknown DNA sequences.

In the Sanger technique, the unknown DNA to be sequenced (known as the "template") is put into solution, and the DNA is denatured, or split into its separate strands, by heating. To the solution is added a short artificially created DNA sequence known as a "primer", the primer corresponding to a small section of the template which is already known. When the solution of denatured template and primer molecules is cooled, the primer adheres to its complementary sequence on the template. Also added to the solution are appropriate polymerase molecules, along with molecules forming the building blocks for the required extension reaction. As the extension reaction proceeds, the bound primer is extended along the length of the template, gradually building up, base by base, an elongate sequence which is the complement of that of the template.

There are four types of building block molecules used in the reaction, each corresponding to one of the bases, A, C, G and T. Specifically, the building blocks are deoxynucleotides known as dATP,dCTP,dGTP and dTTP. Any one of these may be referred to as dNTP. Left to itself, the copying reaction would continue until either the required dNTPs are exhausted, or some extraneous event occurs to stop the reaction. In the Sanger method, a certain proportion of the building blocks are replaced by dideoxynucleotides, namely ddATP, ddCTP, ddGTP and ddTTP (generically ddNTP). If the continuing reaction happens to make use of a dideoxynucleotide from solution, rather than a deoxynucleotide, the molecule binds in the usual way, but all further reaction along that strand is inhibited. Since there is only a relatively small concentration of dideoxynucleotides with the deoxynucleotides, random chance dictates when the reaction on any given chain will be stopped.

Since all copies start at the same position (with the primer), and the stopping position is substantially random, the reaction creates a large number of fragments of cloned DNA for each possible terminating position.

A single vessel charged with template, primer, polymerase, dNTP's and ddNTP's, along with some housekeeping reagents, will give rise to a set of fragments representing each base position in the sequence. Using a single reaction vessel, of course, produces a mixture of all the fragments. The use of four separate reaction volumes, identical except that each contains only one type of terminating ddNTP, ensures that fragments ending in only one of the bases are formed in each volume. The products of each reaction are loaded into a separate lane in a polyacrylamide gel and subject to electrophoresis, causing the fragments to move along the gel. Shorter fragments move more quickly, so the result is an array of fragments laid out along the gel, where each successive group of fragments ends with the next base in the sequence when read up the gel. To ensure that the fragments are visible, an appropriate label must be attached. One method is to attach a radiolabel to one of the dNTP's, ensuring that each fragment on the gel is marked with the radioactive label. Photographic film is placed over the gel, and the mark left on the film by the radioactive decay products are seen in the developed negative as dark bands which can be read off to give the sequence. Alternatively, a fluorescent dye may be attached to the primer, or instead to the dideoxynucleotides.

All methods based on the Sanger technique give rise to measurements which may be represented as four separate graphs, each representing the intensity of a reading from one of the bases on the gel.

The most popular automated DNA sequencing machine in current use, manufactured by ABI, uses a modified version of the Sanger method. To avoid having to use four separate reaction volumes, the dideoxynucleotides are each labelled with one of four types of fluorescent dye, so that each dye is representative of one of the four bases. After the reaction has been completed, the fragments are loaded into a single lane on a gel and sorted by electrophoresis. The gel is then scanned by a laser four times, each scan being via an appropriate narrow bandpass filter which makes only one of the four dyes visible. This accordingly gives rise to four separate traces, which are conventionally plotted on a single graph as a series of peaks, with each of the four bases being represented by a different colour. For any given trace, the presence of a peak at a given relative position represents either the presence of that base at that position, or noise.

By studying the four separate coloured traces and using appropriate peak detection software, one can at least in principle determine the entire sequence of bases within the initial template.

While the methods that have been described above have proved extremely successful in practice, it is believed that there are still improvements which can be made. For example, although automatic sequencers have proved very successful in sequencing DNA, they are now starting to be used for the very much more exacting application of detecting heterozygous mutations in genomic DNA, so as to be able to detect genetic diseases in patients. The mutations that are being looked for are on only one of the patient's two copies of the gene under study, hence what is to be detected is a point in the sequence where, at the corresponding location on the gel, there are two peaks of comparable size indicating that at that position in the DNA the individual has two different copies, one from the normal gene and one from the mutant gene. The degree of peak-to-peak variability seen in typical dye terminator sequencing (using dye labelled dideoxynucleotides) makes this method of limited use for this demanding application. Dye primer sequencing (where the fluorescent dye is attached to the primer) is more useful but is more laborious, as four different reaction volumes have to be used. In any event, there is still a fair amount of peak-to-peak variability, making interpretation of results difficult.

The traditional approach in the past has been to try to reduce the peak-to-peak variability by "improving" the chemistry of the reaction. Such approaches have had only limited success. However, it is known that the peak-to-peak variability is not generally random. When the same DNA fragment from a number of patients is sequenced, for example, the same pattern of variability is seen in each case. Recently, Lipshutz et al have proposed an experimental methodology by which, they say, sequencing accuracy can be improved; see Genomics 19, 417–424(1994).

Lipshutz proposes the setting up of a database having a large number of records, each record consisting of a particular base sequence in a DNA chain along with information on the expected peak heights that are produced by that particular base sequence. The database is in practice set up experimentally, by sequencing large amounts of DNA using conventional automated sequencing methods, followed by a further check by a human operator the purpose of which is to correct any sequencing errors. The determined sequence is then split up into all possible 5-tuples, with each 5-tuple and its corresponding measured peak heights representing one record in the database. The information in the database was then analysed to determine how the peak height in any given position of the 5-tuple varied as a function of the peak height in the other four positions. Using this information, four separate classification trees were constructed, respectively corresponding to those 5-tuples in which the maximum peak height in position five was T,A,C and G. Each classification tree consisted of a sequence of binary tests, which were either be true or false; most of these tests being dependent upon trace heights and/or trace height ratios. To check the correctness of a given base, determined by the conventional sequencer software, the appropriate tree was chosen according to the height of the trace in the fifth position, and the tree was traversed. The result was a confidence measure of the accuracy of the original determination of the particular base at that position.

Although the Lipshutz method is claimed to increase the accuracy of base determinations in the sequence, very substantial problems still remain. Firstly, the improvement in accuracy is not particularly great, and is certainly not believed by the present applicants to be enough to enable the method to be applied to the routine detection of heterozygous mutations in genomic DNA. Secondly, the method relies entirely upon the large experimental database, which would have to be recreated entirely if for example the researcher wanted slightly to change the chemistry used, or to investigate sequences for which the appropriate 5-tuple experimental data are not available. Thirdly, the setting up of the database and the calculation of the classification trees requires both a large amount of experimental work and also a large amount of computing effort. The obvious way of attempting to improve the accuracy of the method—to create an even larger database of 6-tuples—would probably be both experimentally and computationally unfeasible, particularly since such a database would still only be useful for a given chemistry. Finally, the method is computationally inefficient since it considers all possibilities for each position, regardless of whether or not some of those possibilities might already be known to be unlikely or impossible from information which has already been obtained.

We now turn to a brief discussion of the reasons for the peak-to-peak variability (none of which, it is to be noted, are reflected in the Lipshutz' proposals). The fact that the peak-to-peak variability is not random, and indeed seems to remain consistent regardless of the chemistry used, was noted by Larder et al, in their paper Quantitative detection of HIV-1 drug resistance mutations by automated DNA sequencing: *Nature* Oct. 14 1993, pages 671–673. Two primary mechanisms thought to be responsible for peak-to-peak variability are the replication effect, and the fluorescence effect.

The fluorescence effect occurs since the measured fluorescence of the dye depends upon the sequence of bases adjacent to the point in the DNA molecule to which it is bound. When the dye binds to DNA, the dye is partially partitioned from the damping effect of the solvent, and it interacts with the DNA molecule itself. The degree of partitioning and the exact character of the interaction depends upon the nature of the DNA, and hence on the local base sequence. Thus, the fluorescence of the dye molecule is typically determined by the base sequence which leads up to the terminator.

The replication effect is a statistical effect. Simply put, the random nature of the replication stopping process means that the probability of the sequence being stopped at any particular position depends upon how far down the sequence that position is. There will be more shorter sequences, for example, than longer sequences which means that peaks near to the primer are likely to be larger than peaks which are further away from the primer. This effect has been analytically studied by Lee et al in *Nucleic Acids Research*, Vol. 20, No. 10 2471–2483, in a paper entitled DNA sequencing with dye-labelled terminators and T7 DNA polymerase: effects of dyes and dNTPs on incorporation of dye-terminators and probability analysis of termination fragments.

One normally expects to see larger peak-to-peak variability when using dye terminator chemistry then when using dye primer chemistry, since in the latter case there is of course no added variability due to the fluorescence effect.

It is an object of the invention at least to alleviate the difficulties of the prior art.

It is a further object to provide an improved method of automated DNA sequencing in which sequencing errors are reduced.

It is a further object (at least of a restricted form of the invention) to provide a method which is capable of the automated DNA sequencing of heterozygous mutations in genomic DNA. A linked object (again in some restricted versions of the invention) is the creation of a method which is capable of separating mixtures of DNA fragments, for example of providing two separate DNA sequences from a blood sample which contains an admixture of the blood of two separate individuals.

According to the present invention there is provided a method of automatically sequencing a DNA strand, comprising:

a) experimentally determining, for each position in the strand, a measurement representative of a base at that position; and b) starting with an initial sequence comprising a part of the strand where the bases are assumed known, repeatedly building bases onto a growing sequence; and at each step determining a new base to add to a new position in the growing sequence in dependence upon both the measurement at the new position and upon at least some of the previously-determined bases in the growing sequence.

The particular algorithm to be used in carrying out this method should be well within the capabilities of a notional skilled man in this field. Typically, a tree of possibilities needs to be covered, and the tree could either be grown first and then searched or, more efficiently, grown and searched at the same time. Either a parallel or sequential implementation is envisaged and using either recursive or non-recursive code.

Preferably, the method includes, at each step, predicting the measurement at the new position, comparing the predicted measurement with the actual measurement at the new position, and determining the new base as a result of the comparison. The predicted measurement may be calculated based on at least some of the previously-determined bases in the growing sequence. The present applicants have found that making predictions as a function of previously-determined bases, rather than as a function of the actual measurements themselves (heights of traces in the preferred embodiment), one obtains more accuracy and stability, with less prospect of individual errors propagating themselves along the sequence. The effect is so strong that it is in fact preferred that none whatever of the measured values are used in predicting the value for the next position.

The predicted measurement for the new position may comprise four separate values, one for each of the possible bases C, G, A and T. Likewise, the measurement at each position may comprise four separate values, one for each possible base at that position. In the preferred embodiment, the measurements take the form of four separate traces on a graph, one for each of the bases. Four individual values for each position are then determined by measuring the height of each of the traces at that position.

In order to speed up the algorithm, and to ensure that time is not wasted in considering impossible base candidates for a particular position, the method may automatically reject a base as a candidate for the new position if its actual value for that position is less than an expected minimum value. The expected minimum value is calculated as a function of the predicted value for that base at that position; for example, the minimum value might equal the predicted value, or it might instead be a fixed proportion of it such as one half.

In the most straightforward form of the method, the growing sequence may be created base by base, with the new base to be added being next in the sequence to the last previous base added. However, the method does not depend upon every possible base being decodeable, and if for example one or two of the bases are unreadable the algorithm may be designed simply to skip over them and to continue on the far side. That is possible, since the bases on the far side can still be predicted (although with less accuracy) from the bases which are already known.

The growing sequence will normally grow in one direction from the initial sequence, but it could also be arranged to grow in both directions. In addition, there may be a plurality of starting initial sequences, so that there are a plurality of growing sequences. These simply grow simultaneously, in one or both directions, until they link up with each other. The algorithm in this case may involve a graph structure comprising trees which grow both downwardly and upwardly from multiple nucleation points to meet at a plurality of nodes.

The algorithm may include a "lookahead" capability, enabling it to consider a variety of different hypotheses for future bases before finally deciding upon the particular base that is currently being considered. To that end, the method may include at a given step hypothesising the next possible base, then looking ahead to the next step, hypothesising the possible next base for that step, and determining the new base for the given step at least partially in dependence upon a preferred hypothesised base for the next step. Alternatively or in addition, the method may include at a given step looking ahead a plurality of steps, hypothesising a plurality of possible base sequences, and determining the new base for the given step at least partially in dependence upon a preferred hypothesised base sequence.

At each step, the next base to be chosen depends typically upon at least several previously determined bases in the sequence and (depending upon the chemistry) possibly several subsequent positions in the sequence as well. The base to be chosen is that which provides the best fit with the measurements for the sequence as a whole. To that end, at each step an error measure may be constructed which is based upon the predicted measurement and the actual measurement at the new position, an accumulated error measure being kept for at least a part of the growing sequence, and the new base being determined according to the particular base that minimises the accumulated error measure.

In principle, information on all of the previously-determined bases could be used to find the "best" current base, along with (if lookahead is being used) one, two or even more hypothesised bases in the sequence yet to come. Of course, having to check back to the beginning of the sequence each time, and having to make large numbers of lookahead hypotheses uses a large amount of computer time. In practice, the lookahead levels are likely to be restricted, and the number of previously-determined bases which are allowed to contribute to the calculation of the current predicted measurement is likely to be restricted also. Accordingly, in most practical embodiments the accumulated error measure would be kept only for a part of the growing sequence, perhaps for that part which is a fixed number of bases prior to the current base to be determined.

The base to be chosen may be that base which minimises the accumulated error measure of the entire sequence to date or, if lookahead is being used, the accumulated error measure of the determined sequence to date and the preferred hypothesised lookahead sequence.

Depending upon the chemistry that is used in the measurements, the predicted measurement for the new position may be calculated either by using a mathematical model or using a look-up table to simulate the physical effects which are expected. In particular, the algorithm may use a model or look-up table to simulate the replication effect. If terminator chemistry is used, for example with dye-labelled terminators, the method may include a mathematical model or a look-up table to simulate the fluorescence effect.

On occasions, the chemistry may not be exactly known, but it may be possible to predict the steepness and magnitude of the traces or other measurements. In that case, a profile-fitting algorithm may be used in which the preferred hypothesised base sequence may be determined as that sequence which best fits a predicted measurement profile corresponding to the respective positions of the hypothesised base sequence.

An important subsidiary feature of the present invention concerns the detection of DNA heterozygosity. The method used is exactly the same as that used for routine DNA sequencing, except that at each step strands from both alleles are considered at once. Accordingly, using the bases that have already been determined (on both of the alleles) the algorithm proceeds to make a prediction of the expected measurement that will be found, at this position, on each allele. The predictions are compared with the actual measurements, and bases are then assigned, at the current position, to both of the alleles at once. Normally, both of the bases at any given position will be the same, but occasionally, because of a mutation, there may be differences.

The invention also extends to a method of sequencing a mixture of separate DNA strands, again simultaneously dealing with each of the strands using the method as previously described.

The invention further extends to a method of determining the characteristics of a fetus of a pregnant female comprising obtaining a sample from the female, the sample including fetal cells, and automatically sequencing a DNA strand derived from the fetal cells using a method as previously described.

The invention further extends to a method of detecting foreign DNA in a body sample comprising sequencing DNA strands in the sample using a method as previously described, and determining whether foreign DNA is present by comparing the sequenced DNA strands from the sample with sequenced DNA strands derived from a further body sample known to have no foreign DNA.

The invention further extends to a method of determining the relative proportions of a first body sample and a second body sample in an admixed sample, the method comprising sequencing DNA strands in the admixed sample using a method as previously described, determining the relative proportions of DNA from the first sample and from the second sample, and determining the relative proportions of the body samples from the relative proportions of DNA.

It is to be understood that the method is not restricted to any particular chemistry. It can be used both when the primer is labelled, and when the terminators are labelled. The exact labelling is a matter for experiment: possibilities include fluorescent labelling, radioactive labelling and chemiluminescent labelling. Although current automatic sequencers may use DNA fragments which are size fractionated on a polyacrylamide gel, which is then scanned by a laser, that is not essential to the present invention and all that is required is some automated mechanism for providing measurements on a strand of DNA, the measurements being representative of the individual bases along the strand. The preferred method is the Sanger method.

There are a number of specific advantages which flow from the present invention, either in its broadest form or in one of its more restricted versions. The method provides:
1. Considerably improved accuracy in routine genome sequencing applications.
2. The opening up of this rapid and powerful DNA analysis technology to the screening for human mutations. This may take this technology to the stage where it becomes the method of choice for clinical DNA analysis.
3. Increased sensitivity of detection of contaminating DNA in samples extracted from tissues. This may have important forensic applications where samples from one individual are mixed with another, since the method described is capable of individually recognising and sequencing entirely separate DNA strands.
4. Reduced cost of sequencing applications, as the more time-consuming dye primer chemistry would no longer be necessary. All sequencing applications using the method described have improved accuracy, thereby reducing the need to repeat sequencing to check for potential mistakes.

As discussed above, the present invention permits not only the detection of heterozygous mutations but also allows DNA sequences to be determined where there is an admixture of two or more separate DNA sequences. The invention permits the detection of DNA variation in a much smaller fraction than 50% of the total sample DNA. This provides a number of specific advantages, as set out below.

The present invention is capable of detecting chromosomal abnormalities, the most important of which is trisomy 21 (Down syndrome). While a diagnosis of Down Syndrome could be made efficiently by applying the present invention to fetal cells obtained by current invasive sampling methods (for instance amniocentesis or chorionic villus sampling) it is preferred that diagnosis is instead based upon detection of abnormalities in fetal cells present in the maternal circulation or in maternal cervical mucus.

Significant numbers of fetal cells are present in the maternal circulation from week 6 of gestation. These can be concentrated from a maternal venous blood sample using magnetic beads coated with fetal cell-specific antibody to constitute 5–10% of total DNA bound to the beads. It is believed that the present invention is in principle sensitive enough to detect mutations in fetal DNA and/or to detect different copy numbers of normal sequence (in the case of chromosomal abnormalities). This would enable the method of the present invention to replace existing methods of ante-natal DNA testing which involve invasive surgical procedures (for example amniocentesis or chorionic villus sampling) and which carry small but definite risks to morbidity and mortality to both mother and fetus. The method of the present invention may be carried out, in its preferred form, by means of a simple venesection, carrying practically no risk, and is likely to be considerably cheaper than present methods. An alternative potential source of fetal DNA comes from fetal cells obtained from maternal cervical mucus (from 8 to 10 weeks). This is also relatively non-invasive, cheap, and would carry minimal risk.

The method of the present invention may also be applied in situations where it is important to monitor quantitation of residual disease, for example in chronic myelogenous leukaemia where the quantity of tumour cells circulating could be assayed by comparison of tumour-specific and normal patient sequences. In addition, quantitation of load of a pathogen (such as a virus or bacterium) as a proportion of total cellular DNA may be determined. An application of particular interest is in the quantitation of human immuno-deficiency virus (HIV) before and during therapy to provide both prognostic indicators and allowing quantitation of efficiency of treatment.

The invention may be carried into practice in a number of ways and several specific embodiments will now be described, by way of example, with reference to the accompanying drawings, in which:

Figure 1:
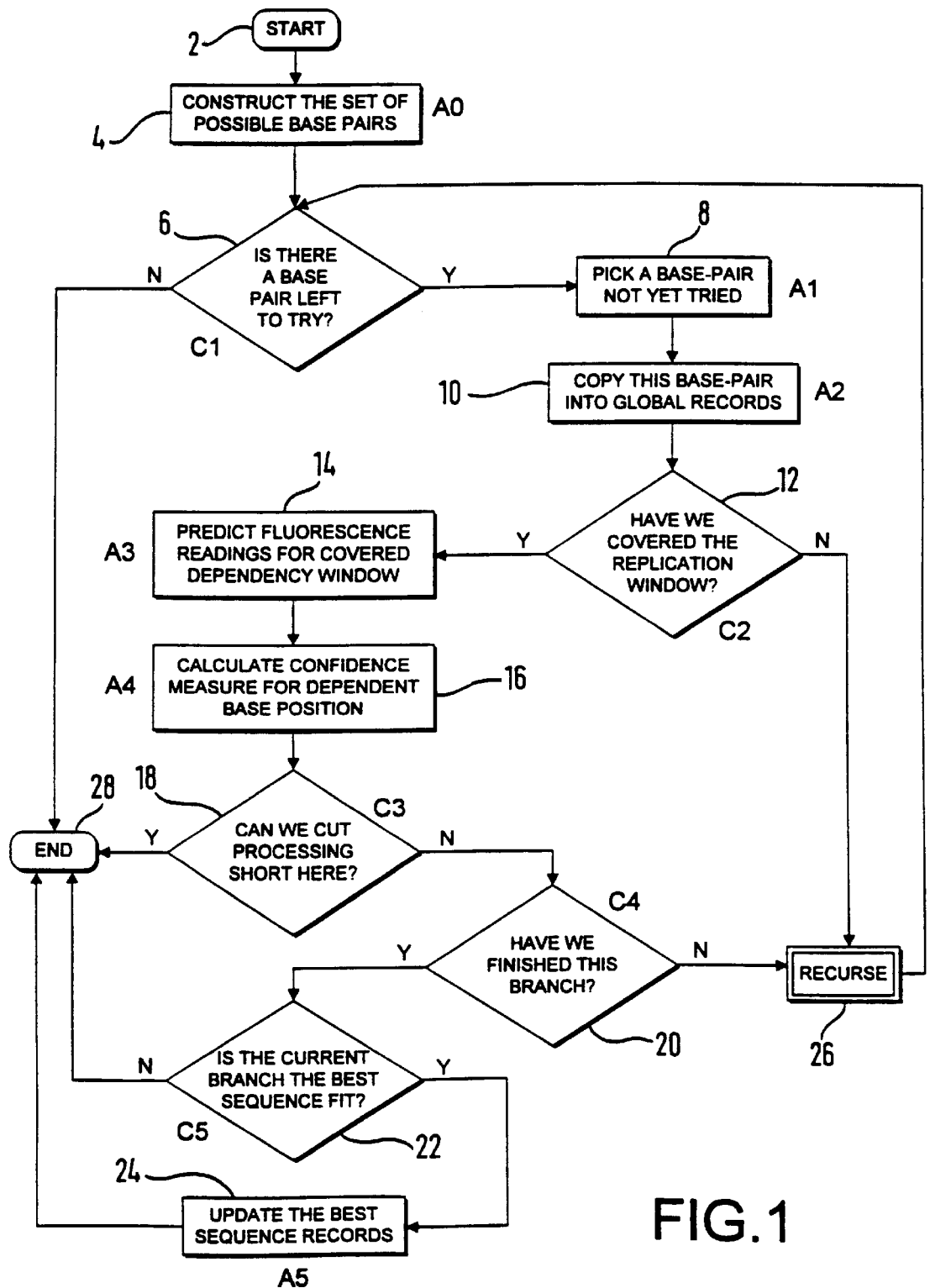
FIG. 1 is a flow diagram showing a sequential recursive algorithm which embodies the present invention.

The present invention makes use of an iterative inductive algorithm which attempts to build up the sequence, base by base, at each point making use of information on bases that have previously been determined. The sequencing always starts with a known short sequence (corresponding to the artificially-created primer molecule) thereby providing a firm base for future induction. As the sequence is constructed, base by base, information on previously-determined and relatively certain bases is used to provide information as to the next probable base in the sequence.

All of the algorithms to be described here could in principle be used for all DNA sequencing applications. In the specific case of detection of heterozygous mutations from genomic DNA amplified by the polymerase chain reaction, one needs to simultaneously sequence both of the two different alleles. The bases on each allele will be the same except where there is a mutation or polymorphism. In that case what one sees on the trace is two peaks in two separate channels. Such an effect cannot accurately be dealt with by current algorithms.

When the algorithms to be described are used for routine sequencing, they attempt at each stage to determine whether the next base in the sequence is an A, C, G or T. In the case of detection of heterozygous mutations, on the other hand, they deal with both alleles at once and they attempt to determine whether the respective bases in the first and second alleles are, for example, AA, CC, GG or TT. They will also consider whether there may be a mutation and, for example, whether the first and second alleles may respectively have bases AC, AG, AT, or indeed any other combination.

It will be understood that complications may occur in the heterozygous case, where one encounters clusters of mutations. If there is a single mutation within a codon (a group of three bases) there is no ambiguity; so for example if the algorithm determines that the bases on the two alleles in the first position are AA, that the bases in the second position are GG and the bases in the third position are AC, we know that there must be a mutation in the third position with the codon in the first allele being AGC and the codon in the second allele being AGA.

Ambiguities may arise, however, when there are two or more mutations next to each other. Such an ambiguity arises, for example, where the algorithm determines that the bases in the first position are AA, the bases in the second position are GT and the bases in the third position are CA. Here, there are two possibilities: either the individual alleles may be AGC and ATA or they may be ATC and AGA.

The methods to be described can deal with these ambiguities since, as the sequence is being constructed on each of the individual alleles, error terms are accumulated which will give a confidence measure for the complete sequence. This may be compared with other, possible, sequences to decide on the correct result, including the inter-allele allocation of the elements of mutations.

Any appropriate inductive algorithm may be used, there being just two requirements: that the algorithm has some way of searching systematically through all the possibilities which present themselves, and that some means can be provided for obtaining a confidence measure as to the correctness of a base or bases at a particular position, as a function of some or all of the bases which have previously been sequenced.

One method of searching through the possible sequences is to construct a tree in which each node is a representation of the base (or in the heterozygous case, bases) present at a given position in the sequence. The root of the tree is the first base (or bases) in the sequence. A child of a node is a possible next element of the sequence. If a particular node has more than one child, this represents the fact that the bases at the next following position may be chosen from a set of different possibilities. A path through the tree from the root to a leaf represents a possible total sequence. The algorithm determines the correct path through the tree using the inference mechanism previously described, at each point making an inference as to the next base (or bases) in the sequence as a function of a confidence measure which is itself based upon some or all of the previously determined nodes.

To determine the confidence measures, one may set up functions which model and simulate the replication effect, for example using the model disclosed in the Lee paper, along with the fluorescence effect (applicable only if dye-terminator chemistry is being used). Alternatively, either or both of these effects could be modelled empirically, for example by way of a simple look-up table determined from prior experimentation. This is in fact relatively easy to do, as there are a relatively small number of combinations to be considered.

One particular difficulty is that although the fluorescence effect depends only on the sequence before the measured base, the replication effect depends on the sequence both before and after the measured base on the template. This introduces a slight complication in that the algorithm ideally has to be capable of looking ahead at least one position in the sequence and investigating what effect the base in the next position might have before deciding definitely on the correct interpretation of the present position.

In practice, the preferred algorithm checks each possibility for the required base positions in the sequence after the measurement point to find that which most closely agrees with the measurements. The results of such a search of the space of local sequences can be used to ascribe a confidence measure to a single base position without reference to other measurements. In the general case, however, we can expect noise to cause readings which might agree more closely with predictions than the sequence peaks. The fact that the base at any position has an effect on the readings a number of positions to either side can be used to avoid this problem.

At any position in the sequence where sufficient of the surrounding sequence is known in order to determine (or look up) the replication and fluorescence effects, we can judge the likelihood of a peak representing that position in the sequence by calculating the measurement we expect at that position, and comparing it with the real reading. We can define an error function which we use to ascribe a degree of confidence to a particular hypothesis of the sequence at any given point.

Figure 2:
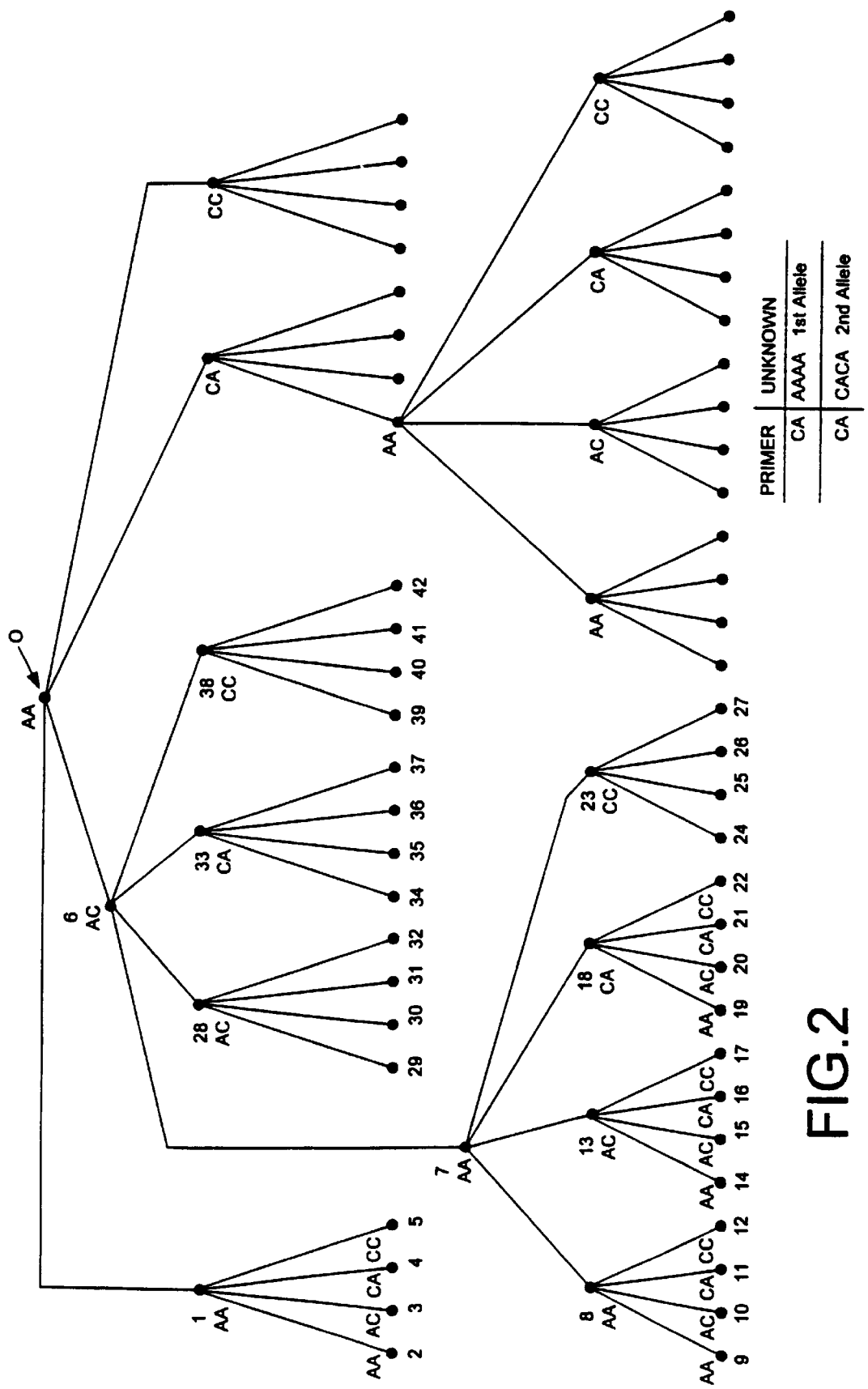
FIG. 2 shows an exemplary tree, and indicates how such a tree may be searched.

FIG. 1 shows, schematically, a preferred recursive algorithm for constructing a searching tree, shown in FIG. 2. The algorithm incorporates a "lookahead" or "blind path" feature, allowing it to try out tentative possibilities for bases yet to be reached within the sequence, thereby allowing a more accurate model of the replication effect to be used. We have found in practice that a look-ahead of one position is normally quite sufficient, but a look-ahead of two or more positions would be quite possible. The algorithm constructs the tree as it occurs, making the necessary look-ahead speculations where necessary. At any point in the tree of initial partial sequences, we can verify readings a number of steps back up the tree equal to the number of bases to the right of the extension point required by our modelling of the replication effect. If the replication effect depends, for example, on two bases either side of the base to be added, the look-ahead will have to be two levels.

Considering a single path in the tree, we step along the sequence constructing the expected measurements as we go, and comparing these with the actual measurements. The comparison, for a single position, is simply the error squared. The individual errors are then added to give a single error or confidence measure for the sequence as a whole. The same test is carried out on other possible sequences, and the chosen sequence is that with the smallest overall error.

To make the search more efficient, paths where the real readings are smaller than those which are predicted can be rejected, as noise will cause a peak to be strictly larger. In a practical embodiment one would probably want to allow for measuring and other systematic errors by skipping paths only where the real reading is some fraction (less than 1) of the expected reading.

We now turn to a more detailed discussion of the preferred algorithm, shown schematically in FIG. 1. The flowchart illustrated represents the sequence of steps that is carried out at a given position in the sequence when attempting to determine what the two allele bases in that position in fact are (for the purpose of this illustration, we are assuming heterozygosity).

The system starts at step 2, and at step 4 at least notionally constructs the set of possible base pairs that could be applicable. In this context, the base pairs are the sequenced bases at the given position on each allele. There are accordingly sixteen possible base pairs, namely: AA, CA, GA, TA, AC, CC, GC, TC, AG, CG, GG, TG, AT, CT, GT, TT. Each of these pairs is unique, as the base on the left appears on a given allele, and the base on the right appears on the other. Thus, GA is distinct from AG. We will refer to a particular pair of bases to be evaluated as the "hypothesis".

It will be understood that step 4 is never explicitly executed: it simply represents the possible set of base pair hypothesis that are to be tried.

At step 6, the algorithm determines whether there is a hypothesis still left to be tried. If not, the algorithm ends immediately; if so, it moves onto step 8 where a hypothesis which has not yet been chosen is selected. This base pair hypothesis is then copied into the global record at step 10. Each cell in the recursion has access to a global record of the sequence which has been hypothesised so far. Each cell is responsible for recording its hypothesis for its own child cells. Accordingly, in this implementation, before a cell can spawn a child, it must copy its local hypothesis into the global record.

At step 12, the algorithm determines whether the replication window has been fully covered. The "replication window" is that part of the sequence, on either side of the current position, in which replication effects are assumed to be non-negligible. Because of the replication effect, it is necessary to hypothesise ahead of the position for which measurements are to be predicted. Thus, at the start of the sequence the algorithm must first build a "blind" or "look-ahead" tree of hypotheses to a depth sufficient to cover the right-hand side of the replication window. If the window has not been covered, then the algorithm recurses at step 26. This involves calling up another copy of the entire routine in order to construct the next deeper level in the hypothesis tree. This next deeper level will, at this point, be branching from this cell's current node in the tree.

Once the replication window has been fully covered, the algorithm moves to step 14 in which the fluorescence reading for the covered dependency window is predicted. This involves a calculation of the number of DNA fragments made, of the required length, the intensity of fluorescence per fragment, and hence the expected fluorescence reading.

At step 16, the confidence measure for the dependent base position is then determined. Here, the algorithm has a prediction for the measurement, and the measurement itself, and accordingly compares the two. There are a number of ways of effecting a confidence reading, but in this implementation if the real reading is lower than the prediction, we are assumed to have zero confidence in it. It is assumed, for this purpose, that all noise is positive additive, and that readings higher than the prediction are ascribed a lower confidence in proportion to the square of the distance.

At step 18, a test is made to see whether the processing can be cut short here. If the confidence level is zero, then there is no need to continue, so the algorithm simply exits this cell.

If the processing cannot be cut short here, control passes to step 20 at which a test is made as to whether this particular branch has been finished. There is a certain depth to which we must recurse, which is determined by the amount of sequence that has to be calculated in a single run. Many factors may affect this choice. Clearly, the limiting factor is likely to be the number of base positions for which there are readings. The depth to which we recurse is greater than the number of base positions to be decoded by the width of the right hand side of the replication window. If the branch has not yet been finished, a further recursion is needed.

Once the branch has been finished, there is a further test at step 22 to determine whether the current branch is the best sequence fit. At this point, the current branch has been finished, and all of the confidence measures for it have been accumulated. This accumulated confidence is now compared with that which is associated with the best branch so far. If the new one has a higher confidence limit than the previous best, the best sequence records are updated at step 24, and the process is completed for this cell. Updating of the best sequence records involves copying the current branch and confidence level into the global record, overwriting the information on the previous best branch.

It is to be understood that the routine shown in FIG. 1 is called with parameters indicating the position in the sequence reached so far, and a measure of the number of templates left still being copied on the current branch. The recurse box indicates a call to the routine itself with the appropriate parameters.

An example of the way in which the routine of FIG. 1 operates in practice may be seen in FIG. 2. This shows the operations that will be carried out in attempting to decode the sequences listed, namely a first allele reading CAAAAA and a second allele reading CACACA. The primer is assumed to be CA, and is of course the same for each allele.

We start at the top of the tree with node 0, with the first position given as CC and the second as AA (here, the first letter of each pair represents the first allele and the second the corresponding position in the second allele).

At node 1, the hypothesis AA is made. Since the replication window has not been covered the procedure recurses to node 2. A hypothesis AA is made for this next position. It is found here that the measurement is smaller than the prediction, so the branch is skipped, and another hypothesis of AC is made at node 3. Again, the measurement is smaller than the prediction so a further hypothesis of CA is made at node 4. The same result is obtained here, and also at node 5, where the hypothesis CC is tried.

As there are no further untried hypotheses depending from node 1, a second hypothesis of AC is made as a possible alternative to the AA of node 1. Again, the dependency window has not been covered, so there is a recursion to node 7 at which the bases AA are hypothesised for the next position in the sequence. That appears to be a possibility, so all of the children of node 7 have to be tried, starting at one level further down with the hypothesis AA at node 8.

Again this seems possible, and nodes 9 to 12 at yet a further level down are tried. In each case, measurement is smaller than prediction, and they are all rejected.

Processing then continues at node 13, where AC is tried as a possible alternative to AA at node 8.

The rest of the tree follows in a similar manner until all of the possibilities have been considered. The chosen sequence is then taken to be the one with the least cumulative error.

It is of course only necessary to recurse the tree as deep as is necessary to decide, at the required level of accuracy, on the correct solution. An alternative method of avoiding recursion of the entire tree is to carry out the sequencing as a collection of overlapping shorter sequences.

In a practical embodiment, the amount of recursion may need to be limited because of time constraints. It is expected, for example, that under normal circumstances a "look-ahead" of one position is likely to be adequate to provide a reasonable modelling of the replication effect. Also, although it may be more accurate to do so, it is not absolutely necessary every time to recurse back to the top of the growing tree. The effect of any given base on a subsequent base in the sequence decreases quite rapidly as the distance between the bases increases. There is therefore in practice likely to be little point in adding up individually each separate contribution to an overall proposed sequence, including the contributions of bases which are far away from the current position. One way of dealing with that problem is to consider bases which are a long way from the current position as effectively being fixed. A tree can then be regrown using, as its root, the nearest point of that fixed sequence.

It will be understood that there are a large number of different algorithms that could be used to achieve the same predictive effect. The only requirement is that it should be possible to determine the next base or bases in the sequence using information derived from previously-determined bases in conjunction with the actual measurements at that position. If the algorithm has a "look-ahead" facility, information may be used on subsequent bases in the sequence, as well as previous bases. Furthermore, the "next" base to be determined need not necessarily be contiguous with the last determined base: using the method already described it would be quite possible, for example, to skip over the positions of two or three bases whose identities are obscured (for example by a blotch of dye on the gel), and to continue on in the usual way. Likewise, with an appropriate tree structure it would be possible to hypothesise forward and backward along the sequence at will.

Additionally, several different primers may be introduced at once to initiate the sequence at several positions. The method described could then hypothesise both forward and backward along the sequence, as appropriate, until the sequences corresponding to the primers become linked up in the overall sequence. This might in practice be done by growing a graph structure similar to the tree shown in FIG. 2, but growing both upwardly and downwardly from multiple nucleation points to meet at many nodes.

The system may further be designed to make use of certain known external information. For example, if the quantities of reagents are known such that the exact size and shape of the traces are known, point predictions may be made. A possible algorithm for this is as follows:

Assume the primer sequence
B: for the next unknown base position in sequence; postulate each possible pair of bases (M,F) in the two alleles
for each (M,F) if we have not covered the right hand side of the replication effect
recurse B: else predict the expected trade readings at this point compare the predictions with the actual measurements make a record of the degree of compliance with the predictions if we can be sure this current branch is unfeasible, jump to next (M,F).
endif if not at end of sequence to be judged, recurse B: else compare this branch with the best so far, and retain the better of the two.
endif
Present the best branch as the result Alternatively, the quantities of the reagents may not be known, so that the steepness and magnitude of the traces may not be known. However, if the ratios of the reagents are known, the general shape and character of the peaked peak variation should be preserved, and the calculation of the replication effect and the fluorescence effect may be by way of a parametric representation.

Alternatively, if the system is described so as to allow the shape of the trace to be predicted, one could match on profile rather than on individual readings by attempting to scale the sequence of prediction. An appropriate algorithm, in which we consider a profile of readings along a whole branch, is as follows:

Assume the primer sequence
B: for the next unknown base position in sequence: postulate each possible pair of bases (M,F) in the two alleles:
if we have not covered the right hand side of the replication effect
recurse B: else for each (M,F), predict the expected trace readings at this point
RECORD THESE READINGS
If not at end of sequence to be judged, recurse B: else
TRANSFORM THE BRANCH PREDICTIONS TO BEST FIT
compare this branch with the best fit so far, and retain the better of the two.
Present the best branch as the result Note that in this case, we cannot make spot decisions about aborting a particular branch until sufficient of the branch is complete reliably to validate a transformed data set.

An additional primer marker may be used on the primer to provide additional information to normalise out the replication effect. If that is done, only the fluorescence effect needs to be covered, so a "lookahead" capability is unnecessary. The two main problems are the avoidance of amplifying up noise signals, and the loss of continuity of dependence throughout the whole sequence.

To normalise a signal, we divide its magnitude by a uniform measure of the number of fragments giving rise to the peak, and this measure is made available by the magnitude of the primer marker peak. Primer peaks for noise or background DNA signals will be small, and therefore will cause the terminator peaks to be heavily magnified if they are regarded as significant.

The main advantage is that processing can be far more local, as the number of fragments does not need to be derived from the previous bases. This improves the availability of effective parallel algorithms.

To improve the speed and effectiveness of the procedure, it would be possible to make use of parallel rather than sequential processing. To take advantage of a number of processors, it is necessary to split the sequence up into sections. The split could either be by sequence position, or by type of base.

Using a parallel system, in which normalisation has been applied, a single base can be determined from a strictly local set of trace data.

Clearly, we must hypothesize any unknown bases, but these may be passed on by other processors as soon as they have derived their own. As well as deciding that a given base position hypothesis is correct, we may also rule out a number of hypotheses. For example, instead of stating that a given position is definitely CA, we might state that it definitely does not include a G on one of the alleles. In general, degrees of confidence in certain results are to be passed between processors, but we may choose to simplify things by asserting correctness if local confidence is sufficiently high, as judged by analysis of a priori dependency information.

With no exogenous information, we have to approach the search for the correct presequence as a graph of possibilities. As information comes in from processors deciding previous base positions necessary for the dependency window to be confidently described, we prune, or lend less weight to, parts of the tree which disagree with that information.

The algorithm on each node may be either recursive, or explicitly based on a tree data structure. The fact that parts of the tree may be discarded at any point means that it is desirable to take steps to avoid wasting processing where possible. The recursive method is most intuitively applied to the depth first search. Of course, anything involving a tree structure can be contrived to operate as a recursion. It is easiest to consider operations on an established tree structure.

For example, an algorithm might be designed along these lines:
(1) First build the tree structure of presequence hypotheses linked across at each depth: (Option: build only those parts of tree which model data can decide immediately).
(2) At each depth of the tree, calculate the confidence measures associated with the branch so far. While this is going on, messages will arrive from other processors which remove parts of the tree, thus abbreviating the processing.

If there are fewer processors available than there are base positions, we choose a scheme of initial allocation which we believe gives the optimum abbreviation of processing.

With the application of such computerised algorithms as these, the peak to peak variability, which has traditionally been regarded by the manufacturers as a problem to be overcome, now becomes an advantage. The variability contains important information which is utilised in the present invention. From the measurements, we are able to derive the total sequence of the DNA on both alleles, thereby simultaneously detecting heterozygosity if present. We are also able to analyse mixtures of entirely separate sequences of DNA. Finally, we obtain a measure of the accuracy of our results.

What is claimed is:

1. A method of automatically sequencing a DNA strand, comprising:
    (a) experimentally determining, for each position in the strand, a measurement representative of a base at that position; and
    (b) starting with an initial sequence comprising a part of the strand where the bases are assumed known, repeatedly building bases onto a growing sequence; and at each step determining a new base to add to a new position in the growing sequence in dependence upon both the measurement at the new position and upon at least some of the previously-determined bases in the growing sequence;
    the method including at each step, predicting the measurement at the new position, comparing the predicted measurement with the actual measurement at the new position, and determining the new base as a result of the comparison.

2. A method of automatically sequencing a DNA strand as claimed in claim 1 in which the predicted measurement for the new position is calculated using a fixed number of the previously-determined bases in the growing sequence.

3. A method of automatically sequencing a DNA strand as claimed in claim 1 in which the predicted measurement for the new position is calculated using at least some of the previously-determined bases in the growing sequence.

4. A method of automatically sequencing a DNA strand as claimed in claim 1 in which the predicted measurement for the new position is calculated without reference to the measurements for any position in the strand.

5. A method of automatically sequencing a DNA strand as claimed in claim 1 in which the predicted measurement for the new position comprises four separate values, one for each possible base.

6. A method of automatically sequencing a DNA strand as claimed in claim 1 in which said measurement at each position comprises four separate values, one for each possible base at that position.

7. A method of automatically sequencing a DNA strand as claimed in claim 6 in which a base is rejected as a candidate for the new position if its actual value for that position is less than an expected minimum value, the expected minimum value being calculated as a function of the predicted measurement for that base at that position.

8. A method of automatically sequencing a DNA strand as claimed in claim 1 in which the growing sequence is created base by base, with the new base to be added being next in the sequence to the last previous base added.

9. A method of automatically sequencing a DNA strand as claimed in claim 1 in which the new base to be added to the growing sequence is not adjacent in the sequence to the last previous base added.

10. A method of automatically sequencing a DNA strand as claimed in claim 1 in which the growing sequence grows in both directions along the strand from the initial sequence.

11. A method of automatically sequencing a DNA strand as claimed in claim 1 including simultaneously growing a plurality of growing sequences from a starting plurality of initial sequences.

12. A method of automatically sequencing a DNA strand as claimed in claim 1 including at a given step, determining the new base for said given step at least partially in dependence upon a preferred hypothetical base, said preferred hypothetical base being determined by looking ahead one step beyond said given step.

13. A method of automatically sequencing a DNA strand as claimed in claim 1 including at a given step looking ahead a plurality of steps, hypothesising a plurality of possible base sequences, and determining the new base for the given step at least partially in dependence upon a preferred hypothesised base sequence.

14. A method of automatically sequencing a DNA strand as claimed in claim 1 in which, at each step, an error measure is constructed based upon the predicted measurement and the actual measurement at the new position, accumulative error measure being kept for at least a part of the growing sequence, and the new base being determined according to the particular base that minimises, the accumulative error measure.

15. A method of automatically sequencing a DNA strand as claimed in claim 12 in which, at each step, an error measure is constructed based upon the predicted measurement and the actual measurement at the new position, accumulative error measure being kept for at least a part of the growing sequence, and the new base being determined according to the particular base that minimises the accumulative error measure, in which the preferred hypothetical base is determined according to the particular base that minimises the accumulative error measure.

16. A method of automatically sequencing a DNA strand as claimed in claim 12 in which, at each step, an error measure is constructed based upon the predicted measurement and the actual measurement at the new position, accumulative error measure being kept for at least a part of the growing sequence, and the new base being determined according to the particular base that minimises the accumulative error measure, and in which the preferred hypothetical base sequence is determined according to the particular sequence that minimises the accumulative error measure.

17. A method of automatically sequencing a DNA strand as claimed in claim 1 in which the Sanger technique is used to experimentally determine, for each position in the strand, the measurement representative of the base at that position.

18. A method of automatically sequencing a DNA strand as claimed in claim 1 in which the measurements are obtained using a modified Sanger technique in which the reaction terminators are each individually labelled according to their respective bases, and in which all are mixed within a single reaction volume.

19. A method of automatically sequencing a DNA strand as claimed in claim 18 in which the reaction primer is also labelled, the information from the primer labels being used to normalise the terminator label measurements.

20. A method of automatically sequencing a DNA strand as claimed in claim 1 in which the predicted measurement for the new position is calculated using a mathematical model or a look-up table which simulates the replication effect.

21. A method of automatically sequencing a DNA strand as claimed in claim 18 in which the reaction terminators are dye-labelled.

22. A method of automatically sequencing a DNA strand as claimed in claim 21 in which the predicted measurement for the new position is calculated using a mathematical model or a look-up table which simulates the fluorescence effect.

23. A method of automatically sequencing a DNA strand as claimed in claim 17 in which the primer is dye-labelled.

24. A method of determining the characteristics of a fetus of a pregnant female comprising obtaining a sample from the female, the sample including fetal cells, and automatically sequencing a DNA strand derived from the fetal cells using a method as claimed in claim 1.

25. A method as claimed in claim 24 in which the sample is a blood sample.

26. A method as claimed in claim 25 in which the sample is a sample of the venous blood of the pregnant female.

27. A method as claimed in claim 24 in which the sample is a mucus sample.

28. A method as claimed in claim 27 in which the sample is a cervical mucus sample.

29. A method as claimed in claim 24 including the step of concentrating the fetal DNA in the sample prior to sequencing.

30. A method as claimed in claim 29 including the step of concentrating the fetal cells in the sample.

31. A method as claimed in claim 30 in which the fetal cells are concentrated by binding them using a cell-specific antibody.

32. A method as claimed in claim 24 in which the determining of the characteristics comprises detecting chromosomal abnormalities.

33. A method as claimed in claim 24 in which the determining of the characteristics comprises detecting DNA mutations.

34. A method of detecting a pathogen in a human or animal patient comprising obtaining a sample from the patient, the sample including the pathogen, and automatically sequencing a DNA strand derived from the pathogen using a method as claimed in claim 1.

35. A method as claimed in claim 34 including the step of determining the quantity of pathogen present by measuring the load of pathogen DNA in the sample.

36. A method as claimed in claim 34 in which the sample is a blood sample.

37. A method as claimed in claim 34 in which the sample is a mucus sample.

38. A method as claimed in claim 34 in which the sample is a urine sample.

39. A method as claimed in claim 34 in which the sample is a semen sample.

40. A method as claimed in claim 34 including the step of concentrating the pathogen DNA in the sample prior to sequencing.

41. A method as claimed in claim 35 in which the load of pathogen DNA is determined as a proportion of the total sample DNA.

42. A method of detecting foreign DNA in a body sample, comprising sequencing DNA strands in the sample using a method as claimed in claim 1 and determining whether foreign DNA is present by comparing the sequenced DNA strands from the sample with sequenced DNA strands derived from a further body sample known to have no foreign DNA.

43. A method of detecting heterozygous sequences, comprising sequencing a pair of DNA strands using a method as claimed in claim 1, at each step simultaneously determining the base pairs to be added to the corresponding positions in the growing sequences.

44. A method of automatically sequencing a mixture of separate DNA strands of a first type and a second type, comprising sequencing the separate strands using a method as claimed in claim 1, at each step determining the base allocations to be added to the corresponding new positions in the growing sequences.

45. A method as claimed in claim 44 including determining the relative proportions of DNA of the first type and of the second type.

46. A method of determining the relative proportions of a first body sample and a second body sample in an admixed sample, the method comprising sequencing DNA strands in the admixed sample using a method as claimed in claim 1 determining the relative proportions of DNA from the first sample and from the second sample, and determining the relative proportions of the body samples from the relative proportions of DNA.

* * * * *